(12) United States Patent
Miyagawa et al.

(10) Patent No.: US 6,468,243 B1
(45) Date of Patent: Oct. 22, 2002

(54) BALLOON CATHETER

(75) Inventors: Katsuya Miyagawa, Osaka (JP); Yoshikazu Kishigami, Osaka (JP); Yuji Tanaka, Osaka (JP)

(73) Assignee: Nipro Corporation, Osaka (JP)

(*) Notice: Subject to any disclaimer, the term of this patent is extended or adjusted under 35 U.S.C. 154(b) by 134 days.

(21) Appl. No.: 09/644,677

(22) Filed: Aug. 24, 2000

(30) Foreign Application Priority Data

Aug. 25, 1999 (JP) .......................... 11-238524

(51) Int. Cl.7 .............................. A61M 29/00
(52) U.S. Cl. .................... 604/96.01; 606/194
(58) Field of Search ................. 604/96.01; 606/194

(56) References Cited

U.S. PATENT DOCUMENTS

| 4,402,307 A | 9/1983 | Hanson et al. ........... 128/1 |
| 5,308,356 A | 5/1994 | Blackshear, Jr. et al. ... 606/194 |
| 5,545,132 A * | 8/1996 | Fagan et al. ........... 604/96.01 |
| 5,730,756 A | 3/1998 | Kieturakis et al. ........ 606/190 |
| 5,792,415 A | 8/1998 | Hijlkema .............. 264/530 |
| 5,853,389 A | 12/1998 | Hijlkema ............... 604/96 |
| 5,868,704 A | 2/1999 | Campbell et al. .......... 604/96 |
| 6,066,100 A | 5/2000 | Willard et al. ........... 600/452 |

FOREIGN PATENT DOCUMENTS

| EP | 0 737 488 A1 | 10/1996 |
| EP | 0 935 973 A2 A3 | 8/1999 |

* cited by examiner

*Primary Examiner*—Ronald Capossela
(74) *Attorney, Agent, or Firm*—Kubovcik & Kubovcik

(57) ABSTRACT

A balloon catheter comprises a shaft 2, a ball-shaped balloon 1 twisted in the form of a screw and mounted on the head of the shaft 2, and a two-way stop cock 5 connected through connection tube 4 with hub 3 on the proximal end of the shaft 2. Injection opening 6 for physiological saline is arranged on the proximal end of the two-way stopcock 5 in order to inflate the balloon. The balloon catheter in the present invention, of which the balloon is of a small diameter during deflation and for which a thinner sheath introducer can be used, can readily occlude a blood vessel.

6 Claims, 5 Drawing Sheets

BALLOON CATHETER

FIELD OF THE INVENTION

The present invention relates to a balloon catheter that is particularly suitable for medical tests carried out using a cardiac catheter.

BACKGROUND OF THE INVENTION

In the cardiac field, recently, catheter therapeutic treatment and a surgical treatment have been carried out. For the therapeutic treatment of the heart, cardiac function and blood flow dynamics must be assessed exactly. In addition to the assessment at a constant state thereof, the assessment of cardiovascular function corresponding to a change under load enables a preliminary assessment of cardiac function and potential lesions. Based on the relationship between ventricular pressure and volume under a decrease of a preload due to a temporary occlusion of the inferior vena cava, for example, there can be deduced a cardiac contraction, a cardiovascular linkage relation and a ventricular energy relation that are not influenced by the load. For such assessment, a balloon catheter is temporarily used to occlude a blood vessel.

As shown in FIG. 4, generally, a small inflatable balloon 10 is mounted on the head of a balloon catheter. By inflating the balloon 10, a blood vessel can be occluded. Generally, the small inflatable balloon 10 is in the shape of a tube (not shown) or a ball (as shown in FIG. 4) when deflated. Since the ball-like balloon is usually made of latex or a rubber-like material such as silicone rubber or polyisoprene, the ball-shape balloon has higher extension and shrinkage. Therefore, the balloon 10 preferably has a ball shape when the diameter of the inflated balloon is required to be 5-fold or more the diameter of the balloon before inflation in order to occlude the blood vessel.

However, the balloon in the shape of a ball has a diameter larger than the balloon in the shape of a tube when deflated. Thus, the deflated balloon in the shape of a ball usually has a diameter of about 2 mm to 5 mm and a thickness of 0.1 mm to 0.5 mm, and is liable to be caught on a check valve or a head of an introducer sheath that inserts the balloon into the body of a patient, so that there is a potential risk of damage to the balloon. When an introducer sheath of a larger size is used so as to avoid such a problem, the risk of damage to the blood vessels, especially the cardiovascular system of a patient is disadvantageously increased.

In U.S. Pat. No. 5,853,389, there is disclosed a balloon for a balloon catheter which comprises a tubular central section and transition sections folded in pleats as urged by spiral ridges on either end of the central section connecting with tubular end sections of less diameter than the central section. But the balloon catheter of this reference is relatively long compared with the diameter thereof, and the introduction into an introducer sheath is troublesome. Further, the deflated diameter of the central section may be more than one fifth of the diameter in a fully inflated condition because the material of the balloon may not be an expandable material such as latex and rubber-like materials and the central section has a plural of pleats as shown in FIG. 6 of this reference.

SUMMARY OF THE INVENTION

Under such circumstances as described above, the present invention has been achieved. It is a purpose of the present invention to provide a balloon catheter which can readily occlude blood vessels, of which the balloon is of a small diameter when deflated, and for which a thinner introducer sheath can be used.

The inventors have made investigations so as to overcome the problems and have thought that by mounting a ball-shaped balloon in the form of a screw on the shaft, the diameter of the balloon when deflated can be put at an optimum dimension. Thus, the present invention has been achieved. More specifically, the present invention relates to a balloon catheter comprising a deflated balloon in the shape of a ball as mounted in the form, or shape, of a screw on a distal end of a shaft. Herein, the balloon in the form of a screw can be mounted by fixing one end of a hollow ball, both ends of which are open on the shaft, modifying the shape of the ball in the form of a screw by twisting the ball and fixing the other end on the shaft.

EMBODIMENT OF THE INVENTION

Examples of the invention will be described on the basis of the drawings.

Figure 1:
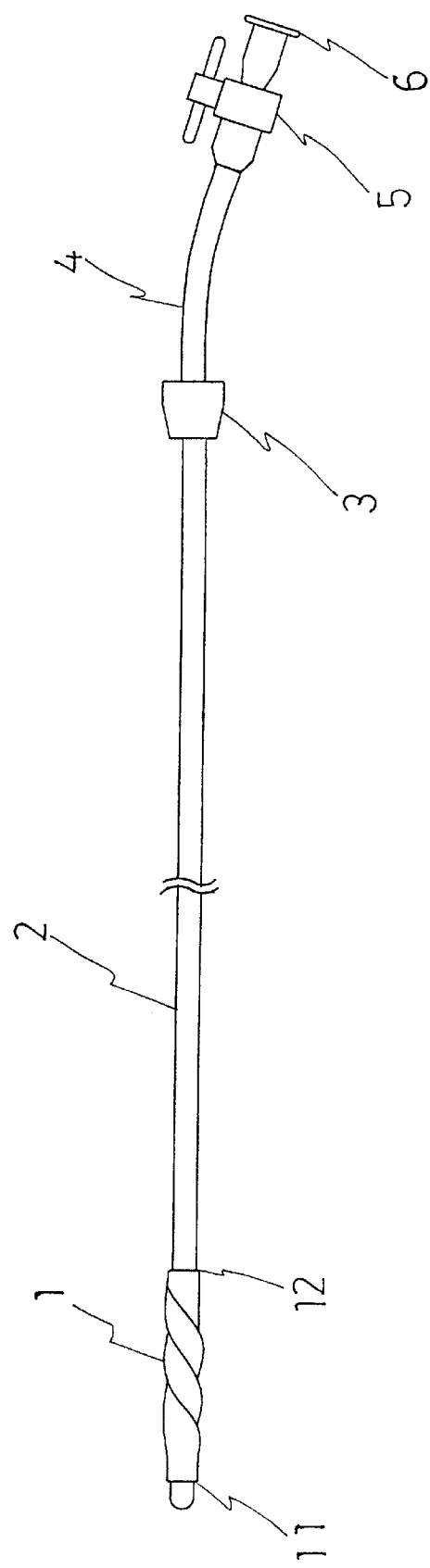
FIG. 1 is a plan view depicting one example of the balloon catheter in the present invention.
Figure 2:
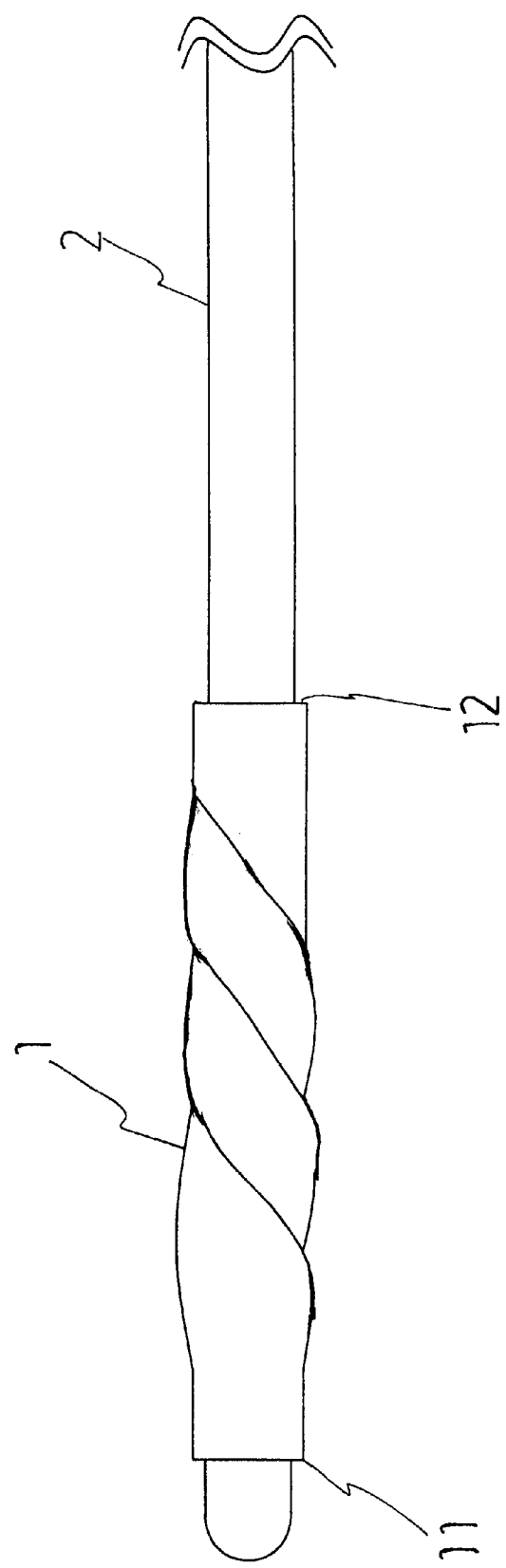
FIG. 2 is an enlarged view of the main part of the balloon catheter as shown in FIG. 1.

As shown in FIGS. 1 and 2, the balloon catheter comprises a shaft 2, a deflated ball-shaped balloon 1 modified to have the form of a screw and mounted on the distal end of the shaft 2, and a two-way stop cock 5 connected through connection tube 4 with hub 3 on the proximal end of the shaft 2. Then, an infusion opening 6 of physiological saline is arranged on the proximal end of the two-way stopcock 5.

The shaft 2 can be inserted from a femoral vein through a sheath introducer (not shown in the figure) into a blood vessel, and is of such hardness that it does not cause damage to the blood vessel. The cross section of shaft 2 is in the form of a circle or a shape close to a circle, while the outer diameter of the shaft 2 is 1 to 2 mm. Lumens (not shown in the figure) for introducing physiological saline to inflate the balloon 1 are formed through the sheath 2. The number of the lumens is determined, depending on necessity. The shaft 2 is satisfactorily formed with a double tube, one of which tubes is a lumen (not shown in the figure) for a guide wire and other is a lumen for introducing physiological saline.

As the materials composing the shaft 2, plastics such as polyolefin, polyamide, polyester, fluoroplastic, silicone resin, polyvinyl chloride and polyurethane, natural rubber, stainless steel and the like can be used.

The balloon 1 can be inflated to a size capable of contacting a wall of the blood vessel thereby blocking blood flow. Because the diameter of the blood vessel is usually about 30 mm at maximum, the outer diameter of the deflated balloon (prior to being modified in the form of a screw) is preferably 2 mm to 5 mm, the thickness of the walls of the deflated balloon is preferably 0.1 mm to 0.5 mm, and the expansion thereof during inflation is preferably about 5- to 8-fold.

As the materials of which such balloon 1 is composed, use is made of synthetic rubbers such as silicone rubber and polyisoprene, natural rubber, latex and the like.

The hollow balloon 1 in the present invention has a ball-shape and two open ends, the inflated diameter is usually 10 to 40 mm.

The balloon 1 can be mounted on the distal end of the shaft 2 by bonding both the open ends of the hollow balloon 1 using an adhesive, for example, cyanoacrylate-type or silicone-type adhesive. More specifically, one open end 12 of the hollow balloon 1 is fixed on a portion distant from the distal end of the shaft 2; the balloon 1 is twisted to modify the shape of the balloon to the form of a screw around the shaft 2, and the other end 11 of the balloon is satisfactorily fixed on the shaft 2.

Figure 5:
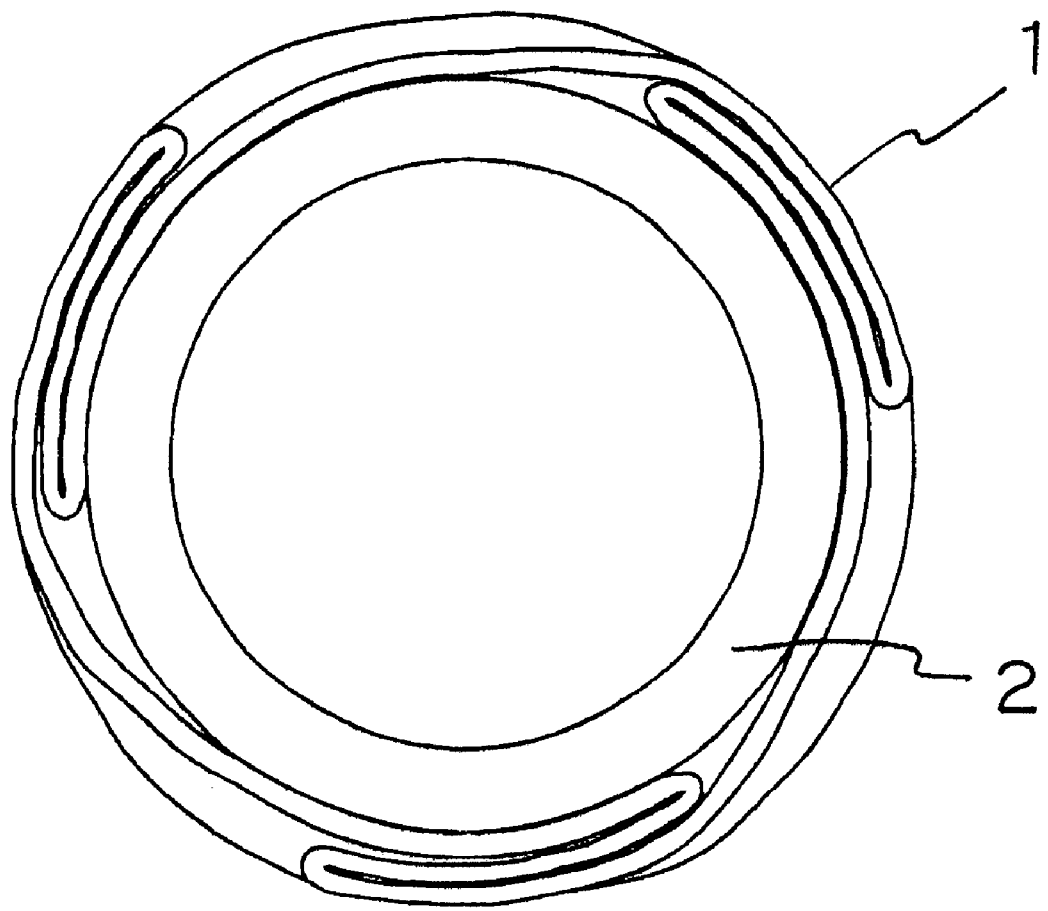
FIG. 5 is a cross-section of the twisted balloon of the balloon catheter as shown in FIG. 2.

The balloon is twisted in a longitudinal direction of the catheter. The twist frequency of the balloon depends on the diameter, but is preferably one to five times. The cross section of the balloon 1 twisted around the shaft 2 is shown in FIG. 5.

The use of the balloon catheter in the present invention is described below.

Figure 3:
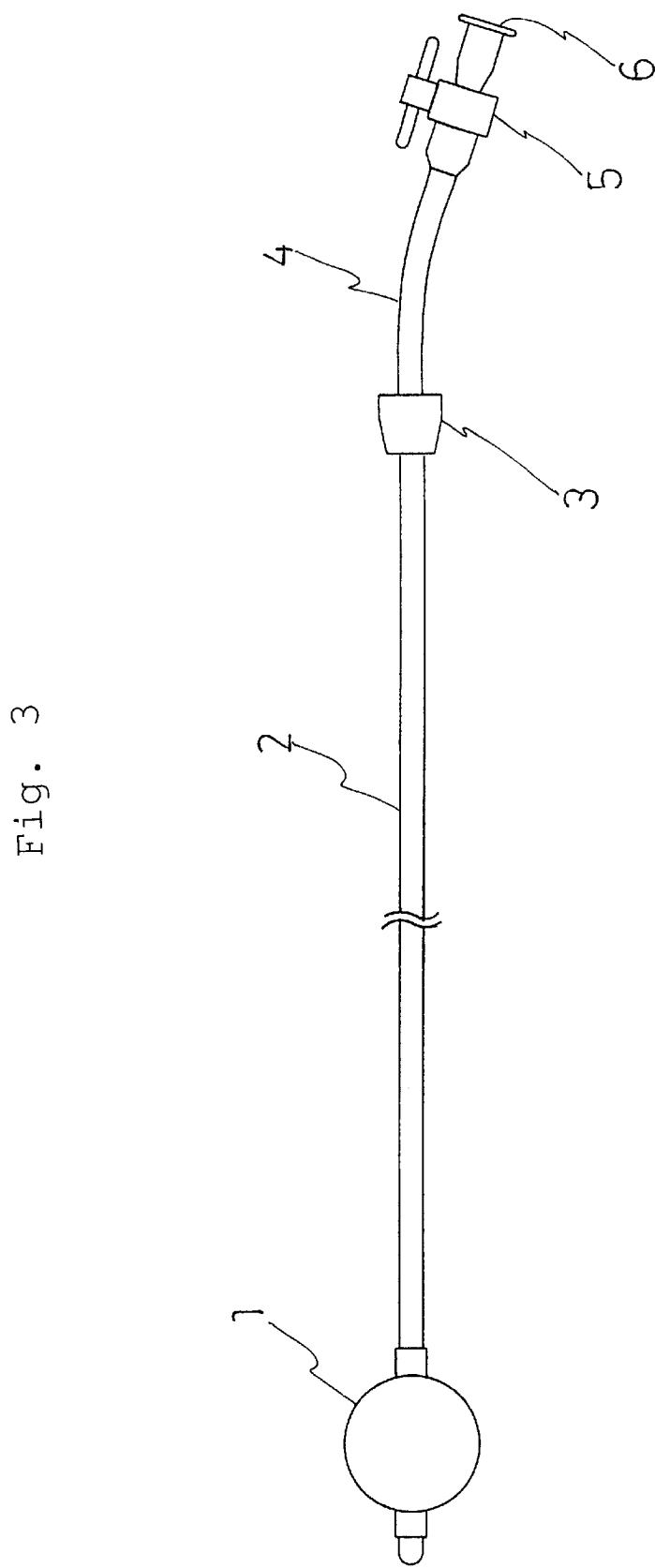
FIG. 3 is a plain view depicting the balloon catheter with inflated balloon.
Figure 4:
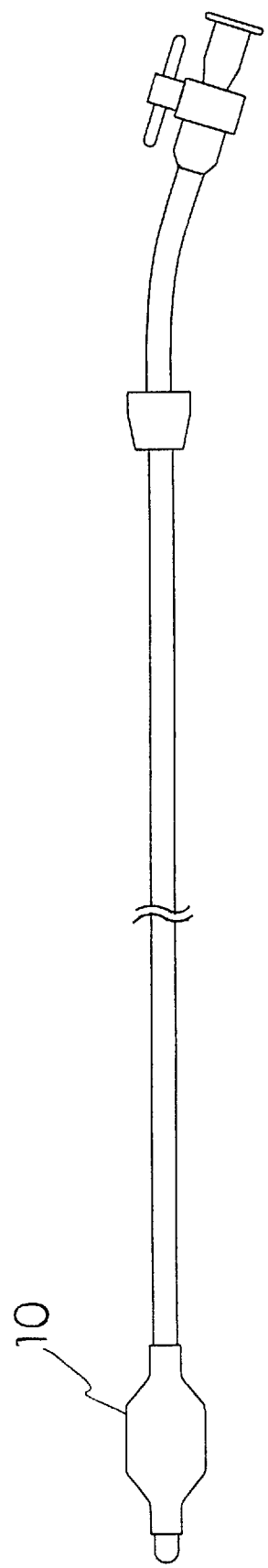
FIG. 4 is a plan view depicting a conventional balloon catheter.

Such a balloon catheter as shown in FIG. 1 is inserted from a femoral vein to transfer the balloon 1 to an intended blood vessel site. After confirming the position in a blood vessel, physiological saline containing, for example, a contrast medium is injected through the lumen (not shown in the figure) into the balloon 1, to expand the balloon as shown in FIG. 3 and thereby occlude the blood vessel. After termination of the procedures, the balloon 1 is deflated to remove the balloon catheter from the blood vessel. Then, the balloon 1 resumes the initial screw form as shown in FIG. 1.

Effects of the Invention

As may be understood from the aforementioned description, the use of the balloon catheter of the present invention enables the reduction of resistance during the insertion and removal of the balloon catheter into the sheath introducer, to thereby avoid damage to the balloon. Additionally because a thinner sheath introducer can be used, damage of a blood vessel by the sheath introducer can be reduced. Further, the deflated balloon can be easily equipped at the distal end of the shaft.

What is claimed is:

1. A balloon catheter comprising a catheter shaft and a balloon mounted on a distal end of the shaft, said balloon having a ball-shape when inflated and being in the form of a screw when deflated and having two open ends, each of said ends being secured to said shaft, wherein said open ends of the balloon as secured to said shaft are twisted one to five times in a longitudinal direction of the catheter shaft relative to their position prior to being secured to the shaft and wherein the balloon when deflated and prior to twisting has a diameter of about 2 mm to 5 mm and a thickness of about 0.1 mm to 0.5 mm and can inflate 5- to 8-times its deflated size.

2. A balloon catheter according to claim 1, further comprising a two-way stop cock connected through a connection tube with a hub on a base end of the shaft.

3. A balloon catheter according to claim 2, wherein said balloon is made of the material selected from the group of synthetic rubber, natural rubber and latex.

4. A balloon catheter according to claim 2, wherein the catheter is suitable for insertion into a cardiovascular system.

5. A balloon catheter according to claim 1, wherein said balloon is made of the material selected from the group of synthetic rubber, natural rubber and latex.

6. A balloon catheter according to claim 1, wherein the catheter is suitable for insertion into a cardiovascular system.

* * * * *